US012440700B2

(12) United States Patent
Martin et al.

(10) Patent No.: US 12,440,700 B2
(45) Date of Patent: Oct. 14, 2025

(54) PHOTOTHERAPY DEVICE

(71) Applicants: Jessi Martin, Stow, OH (US); Timothy Knezevich, Cleveland, OH (US); Tayluer Streat-Ricchiuti, Philadelphia, PA (US); Manaswini Chennoju, Fishers, IN (US)

(72) Inventors: Jessi Martin, Stow, OH (US); Timothy Knezevich, Cleveland, OH (US); Tayluer Streat-Ricchiuti, Philadelphia, PA (US); Manaswini Chennoju, Fishers, IN (US)

(73) Assignees: Jessi Martin, Stow, OH (US); Timothy Knezevich, Cleveland, OH (US); Tayluer Streat-Richhiuti, Philadelphia, PA (US); Manaswini Chennoju, Fishers, IN (US)

( * ) Notice: Subject to any disclaimer, the term of this patent is extended or adjusted under 35 U.S.C. 154(b) by 7 days.

(21) Appl. No.: 18/782,346

(22) Filed: Jul. 24, 2024

(65) Prior Publication Data

US 2024/0374917 A1 Nov. 14, 2024

Related U.S. Application Data

(63) Continuation-in-part of application No. 17/991,637, filed on Nov. 21, 2022, and a continuation of application No. PCT/US2023/080315, filed on Nov. 17, 2023, which is a continuation of application No. 17/991,637, filed on Nov. 21, 2022.

(Continued)

(51) Int. Cl.
*A61N 5/06* (2006.01)
*A61G 11/00* (2006.01)

(52) U.S. Cl.
CPC ............ *A61N 5/0621* (2013.01); *A61G 11/00* (2013.01); *A61N 2005/0637* (2013.01); *A61N 2005/0657* (2013.01); *A61N 2005/0663* (2013.01)

(58) Field of Classification Search
USPC ................................................ 607/1, 88, 95
See application file for complete search history.

(56) References Cited

U.S. PATENT DOCUMENTS 1,946,567 A * 2/1934 Braunworth ........... A47H 99/00 52/63
6,402,681 B1 * 6/2002 McDonough ........ A61N 5/0621 362/130

(Continued)

FOREIGN PATENT DOCUMENTS

CN 113397874 B 10/2022
EP 1247512 B1 * 5/2009 ............. A61G 11/00

OTHER PUBLICATIONS

"Five Oceans, '6-Slotted Louvered Flush Hose Ventilators, 3-Inch, White—F0110', Five Oceans, 2020, https://www.five-oceans.com/products/6-slotted-louvered-flush-hose-ventilators-3-inch-white-fo110-fo-110?_pos=1&_psq=110&_ss=e&_v=1.0" (Year: 2020).*

(Continued)

*Primary Examiner* — Jennifer Pitrak McDonald
*Assistant Examiner* — Michael T. Holtzclaw
(74) *Attorney, Agent, or Firm* — McNees Wallace & Nurick LLC

(57) ABSTRACT

In an exemplary embodiment, a phototherapy device capable of delivering natural sunlight to a subject is provided. The phototherapy device includes a bassinet configured to hold a subject for treatment, an angular non-domed enclosure having an angled front wall and made from a flexible, transparent material connected to the incubator to create a space therein, and in some embodiments a support for supporting the bassinet. The enclosure formed around the bassinet allows visible sunlight to enter the enclosure in any direction for treating the subject while partially filtering ultraviolet (UV) and infrared radiation (IR) rays of the visible sunlight from entering the device, and is configured (Continued)

to direct incident IR rays out of the enclosure such that there is no build-up of heat that would harm the subject resting therein.

18 Claims, 9 Drawing Sheets

Related U.S. Application Data

(60) Provisional application No. 63/282,630, filed on Nov. 23, 2021.

(56) References Cited

U.S. PATENT DOCUMENTS

| | | | | |
|---|---|---|---|---|
| 6,464,715 | B1 | 10/2002 | Gysens et al. | |
| 11,364,167 | B2 * | 6/2022 | Auzelyte | A61G 11/002 |
| 11,439,554 | B2 | 9/2022 | Breegi | |
| 2008/0269844 | A1 * | 10/2008 | Logslett | A61N 5/0621<br>5/663 |
| 2017/0182282 | A1 * | 6/2017 | Rea | A61G 11/00 |
| 2020/0038679 | A1 * | 2/2020 | Brezinski | A61F 7/08 |
| 2020/0179715 | A1 * | 6/2020 | Nelson | A41D 20/00 |

OTHER PUBLICATIONS

Notification of Transmittal of the International Search Report and the Written Opinion of the International Searching Authority, or the Declaration issued to counterpart Application No. PCT/US2023/080315 dated Apr. 10, 2024.

* cited by examiner

PHOTOTHERAPY DEVICE

RELATED APPLICATION

This application is a continuation in part of application of U.S. patent application Ser. No. 17/991,637 filed on Nov. 21, 2022, which claims the benefit of, and priority to, U.S. provisional application 63/282,630, entitled "Phototherapy Device" filed Nov. 23, 2021, and is a continuation application of Patent Cooperation Treaty Application PCT/US2023/080315 filed on Nov. 17, 2023, which is a continuation application of U.S. patent application Ser. No. 17/991,637 filed on Nov. 21, 2022, the entire contents being incorporated by reference herein.

TECHNICAL FIELD

The present disclosure relates to a portable phototherapy device. More specifically, the present disclosure is directed to a portable phototherapy device capable of delivering natural sunlight to a subject.

BACKGROUND

A womb contains a lower oxygen environment than a surrounding environment. To adjust to this environment, a fetus will increase the oxygen carrying capacity through an increase in hemoglobin. When infants are born, the oxygen in their environment increases, and the excess hemoglobin is discarded and converted into bilirubin. When bilirubin is first created from heme in hemoglobin, it is considered unconjugated, as it is fat and not water soluble, and binds to albumin to be processed in a liver and excreted in urine and feces. Neurological tissue has a high affinity for unconjugated bilirubin and can cross the blood-brain barrier. Yet, newborn infants do not possess the ability to process bilirubin through their liver, so an excess of unconjugated bilirubin can build up in the babies' system.

Typically, an infant with a healthy diet of breast milk can process the bilirubin until the liver is developed enough to process the bilirubin on its own. However, 60% of all term newborns and 80% of premature newborns experience a build-up of bilirubin known as hyperbilirubinemia (jaundice) before the full function of the development of the liver. The use of phototherapy either through artificial or natural sunlight is a known effective treatment to reduce the amount of conjugated bilirubin in the infants' body. Phototherapy is effective because certain wavelengths of light can isomerize the unconjugated bilirubin into conjugated bilirubin (which is water-soluble) through the skin and help the infant pass it through their stool. If the levels of bilirubin in the bloodstream become too high, it can cross the blood-brain barrier and cause Kernicterus, a condition involving deposits of bilirubin in the brain. Kernicterus can cause illness or diseases, such as, cerebral palsy, developmental and intellectual delay, hearing deficiencies, dental dysplasia, and/or oculomotor disturbances.

In developing nations, jaundice caused by unconjugated hyperbilirubinemia is still a leading cause of infant mortality and complications. This can be attributed to a lack of electricity to power the phototherapy devices and the risks associated with natural sunlight therapy. While sunlight is readily available, placing newborn infants in sunlight for extended periods of time can risk exposure to skin-damaging UV rays and cause overheating. Additionally, effective natural sunlight phototherapy can be undermined by underexposure due to the fear of overexposure in unprotected sunlight. Ineffective or complete lack of phototherapy allows unconjugated hyperbilirubinemia to progress leading to complications such as kernicterus or even death.

Conventional phototherapy treatment of newborns with jaundice may involve placement of the infant in an isolette tank or incubator with direct use of high-powered lighting (e.g., LED lamps), as shown in FIG. 6A. However, these devices are not optimal in that they generate undesirable amount of heat, are bulky, obtrusive, and not portable. In addition, these devices are not easily rendered effective as the device requires a power source, and thus, the device cannot be moved around easily, nor portable enough to move (i.e., carry) the device indoor or outside with ease.

Other conventional phototherapy devices, as shown in FIG. 6B, may involve a blanket having a sheet of fabric material that includes light emitting devices of a wavelength or wavelengths suitable for treatment of jaundice. An infant can lay on the fabric material or the infant can be tightly wrapped in the sheet of fabric material. However, the fabric material directly touches the infant which can be reactive to the skin of the infant and not porous enough for air circulation. Similarly, the blanket also requires a power source, which is not optimal for portability.

There remains a need to provide an effective phototherapy device for treating hyperbilirubinemia that is easy to transport around and inexpensive to manufacture. The phototherapy device should not require additional equipment(s), power source, maintenance or training to assemble and to operate, and must be particularly useful in areas of remote access, third world, and developing countries, where specific needs may be required.

SUMMARY

In an exemplary embodiment, a phototherapy device capable of delivering natural sunlight to a subject is provided. The phototherapy device includes an incubator configured to hold a subject for treatment, a support for supporting the incubator, and an enclosure made from a flexible, transparent material connected to the incubator to create a space therein. The enclosure formed around the incubator allows visible sunlight to enter the enclosure in any direction for treating the subject while partially filtering ultraviolet (UV) and infrared radiation (IR) rays of the visible sunlight. The enclosure includes an angled front wall made from a first material and a back wall made from a second material different than the first material.

In another exemplary embodiment, a portable phototherapy device capable of delivering natural sunlight to a subject is provided. The portable phototherapy device includes a frame including an upper frame portion and a lower frame portion, and an enclosure including an upper enclosure portion and a lower enclosure portion. The upper frame portion and the lower frame portion include a plurality of rods. The plurality of rods are removable connected to each other. The upper enclosure portion and the lower enclosure portion are made from a flexible, transparent material to filter ultraviolent (UV) and infrared radiation (IR), and the upper enclosure portion can be separable from the lower enclosure portion. The upper frame portion can be framed as a structure to hold the upper enclosure portion and the lower enclosure portion. The lower frame portion can be framed as a structure to hold a bassinet In another exemplary embodiment, a portable phototherapy device capable of delivering natural sunlight is provided. The portable phototherapy device includes a frame including a first frame member and a second frame member, a support for holding a bassinet, and a flexible, transparent material attached to the first frame member and the second frame member to form an enclosure. The first frame member and the second frame member can be moveable with respect to each other causing the portable phototherapy device to be in a first configuration or in a second configuration. The support is positioned between the first frame member and the second frame member. The flexible, transparent material is configured to filter ultraviolet (UV) and infrared radiation (IR) rays of sunlight.

Other features and advantages of the present invention will be apparent from the following more detailed description of the preferred embodiment which illustrates, by way of example, the principles of the invention.

Figure 1:
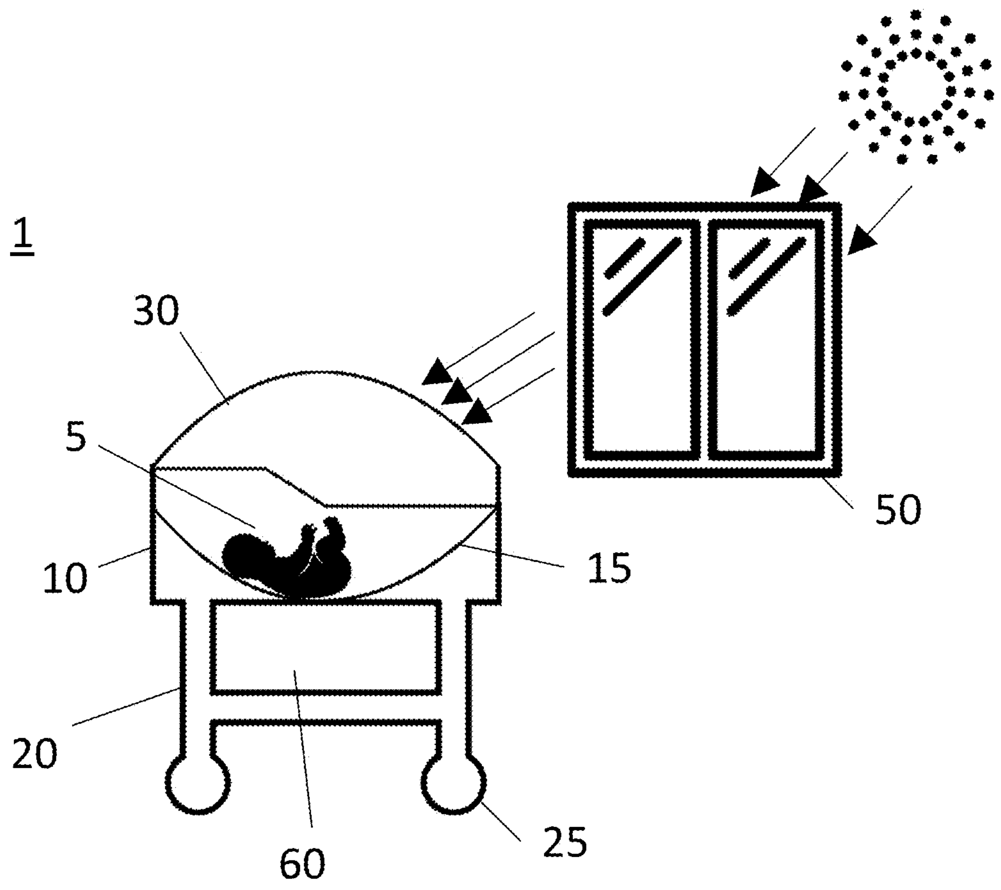
FIG. 1 is a schematic view of a portable phototherapy device, according to an example embodiment of the present disclosure.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

A phototherapy device, according to the present disclosure, is a device that is portable requiring no power source for use. The phototherapy device is lightweight, capable of being flattened, folded, rolled, compressed, or otherwise collapsed, to a size smaller than that of its operating size. The phototherapy device does not require special facilities for use; and allows for easy transport and shipment, as well as "in-home" or "field" application. The phototherapy device is not limited or constrained by any power source. The phototherapy device allows for directed and uninterrupted phototherapy without unduly confining or restricting the infant. While being portable, the phototherapy device is adaptable for fitted use over any pre-existing structure, framework, or device (e.g., infant incubator, crib, or bassinet). Unlike wraparound, or garment-type phototherapy devices, the phototherapy device does not come into physical contact with the infant, thus avoiding any physical distress, harm, or discomfort to the infant, and allowing for proper ventilation and circulation. The phototherapy device also allows caregiver access to the infant without having to operate or manipulate any elements on the device. This allows uninterrupted operation of the phototherapy device. The phototherapy device avoids undesirable conditions such as excessive heat and/or dehydration to the infant.

The phototherapy device is easy, and inexpensive to manufacture, to transport, and to ship. The phototherapy device requires no special facilities, equipment, power requirements, maintenance or training to assemble and to operate, thus making it particularly useful in areas of remote access, third world, and developing countries, where specific needs may be the greatest.

In an exemplary embodiment, a portable phototherapy device capable of delivering natural sunlight to a subject is provided. The portable phototherapy device includes a frame member having an upper frame portion and a lower frame portion and an enclosure having an upper enclosure portion and a lower enclosure portion. The lower frame portion is framed as a structure to hold a bassinet. The upper frame portion is framed as a structure to hold the upper enclosure portion and the lower enclosure portion. Further, the upper frame portion and the lower frame portion include a plurality of rods. The plurality of rods are flexible, semi-rigid to rigid enough to maintain a free-standing configuration. The plurality of rods can be removeable (i.e., disconnected) from each other. This allows for disassembly for easy transport or storage when not in use. Further, the upper enclosure portion can be designed to separate from the lower enclosure portion (i.e., removed with respect to the lower enclosure portion). This feature allows heat to be removed and/or allows a caregiver to handle the infant without disassembling the phototherapy device.

In another exemplary embodiment, the portable phototherapy device includes a frame including a first frame member and a second frame member. In this exemplary embodiment, the frame is capable of being flattened, folded, compressed, or otherwise collapsed, to a size that is less than the working space of the assembled and operational phototherapy device. The frame may be composed of poles, rods, tubes, slats, springs, or the like that can articulate, or can otherwise be positioned one to another such that they can be configured (e.g., "assembled"), with an enclosure, to form the structure of the phototherapy device. The frame can be configured (e.g., folded or disassembled) for easy transport or storage when not in use.

FIG. 1 is a perspective view of a phototherapy device according to an example embodiment. The phototherapy device 1 includes an incubator 10, an enclosure 30 covering the incubator 10, and a bassinet 15 in which an infant 5 is positioned on the bassinet 15. The phototherapy apparatus 1 receives natural sunlight that shines through a window 50 of a building structure. In this case, the phototherapy device 1 can be a distance from the window 50 to receive the natural sunlight. For example, the phototherapy device 1 can be as close as a foot from the window 50 to as far as the natural sunlight reaches the phototherapy device 1. It should be appreciated that any distance may be utilized as long as the natural sunlight reaches the phototherapy device 1 without obtrusion.

It should be appreciated that more than one window 50 may be employed to allow sunlight to reach the phototherapy device 1 in optimal application. This allows greater coverage that the sunlight has reached the phototherapy device 1. For example, the phototherapy device 1 can be next to a wall of a building where the entire wall is made up of windows.

The incubator 10 can be provided (e.g., attached, mounted) on a base 20 that is supported on casters 25 (i.e., wheels). The use of wheels permits the phototherapy device 1 to be a movable base 20, and further allows the phototherapy apparatus 1 to be used with various incubators, cribs, and other infant supporting devices, including various therapy platforms. In other uses, the incubator 10, via the wheels, can be transported closer to the window 50 or in occasion, can be transported outdoor to receive the natural sunlight.

The enclosure 30 is attached to the incubator 10. That is, the enclosure 30 covers the incubator 10. In other words, the enclosure 30 forms a bubble creating a space between the incubator 10 and the enclosure 30 and permits the infant 5 to lie inside of the space. The enclosure 30 wraps entirely (e.g., formed 360°) around the incubator 10. This allows sunlight to reach and enter the enclosure 30 in any or all directions for optimal light phototherapy. To describe in a different manner, due to the formed shaped of the enclosure 30, surface area of light exposure to the infant 5 is increased. In some implementations, a frame (not shown) may be coupled to an upper portion of the incubator 10 to form a structure such that the enclosure 30 encloses the frame and a portion of the incubator 10. The frame ensures the shape of the enclosure 30 attached to the incubator 10. In some implementations, the enclosure 30 may include fastening means to attach the enclosure 30 to the incubator 10. For example, the fastening means can be, but not limited to, zippers, buttons, hook-and-loop fasteners, adhesives, and/or tape. In some implementations, the fastening means can be provided on an outer surface of the incubator 10 such that the enclosure 30 is attached to the incubator 10. For example, there may be fastening means on all four sides of the incubator 10 to ensure a secure attachment.

The enclosure 30 can be made from many materials of various kinds of plastic or polyethylene sheet that is flexible and transparent. The flexible, transparent material filters ultraviolent (UV) and infrared radiation (IR) and constructed to prevent overexposure to the skin of the infant 5. Ordinarily, sunlight is broken down into three major components: (1) visible light, with wavelengths between 400 nanometers (nm) to 700 nanometers (nm), (2) ultraviolet light, with wavelengths shorter than 400 nm, and (3) infrared radiation, with wavelengths longer than 700 nm. To avoid the harmful components of sunlight, the enclosure 30 should receive only the visible light having the wavelengths between 400 nm to 700 nm to transmit the efficacy of monochromatic visible light to the infant 5. The optimal light wavelength range for jaundice treatment is in the blue light spectrum from about 380 nm to 470 nm. In that range, the orange to red bilirubin is able to absorb the maximum amount of light and break down the bilirubin into a form that the body can get rid of through urine and stool. The filtered enclosure 30 helps maintain the infant's unconjugated bilirubin levels from exceeding 20 mg/dL.

In some implementations, the flexible material of the filtered enclosure 30 has properties that is resistant to (enable to withstand) prevent cuts, tears, rips to the flexible material. For example, the flexible material of the filtered enclosure 30 can be made from, but not limited to, polyethylene, polypropylene, and/or polyvinyl chloride.

In some implementations, the flexible material of the filtered enclosure 30 has properties to prevent scratches on a surface of the flexible material, i.e., anti-scratching properties. For example, the anti-scratching properties can be embodied in the flexible material. In another example, the anti-scratching properties can be a coating or layer on an outer surface of the flexible material. The coating can be laminated or laminated together to form the flexible material.

In some implementations, the flexible material of the filtered enclosure 30 has properties to be deformable. That is, the flexible material is formed of a plastically deformable material that is flexible enough to be deformed to a desired configuration by hand while also having sufficient shape memory to retain the configuration to which it has been deformed during subsequent use of the device for delivery of a light therapy session.

The bassinet 15 includes a sheet to hold the infant 5 inside the incubator 10 or placed atop the sheet. The sheet is made from a material in which the material touching the skin of the infant is non-reactive and porous for air circulation, i.e., breathability. In some implementations, the sheet can be made from cloth, a mesh cloth or variation thereof. In one exemplary implementation, the sheet is a mesh pillow case-type cloth. The mesh helps to allow air to pass to/from outside of the incubator 10 to the infant 5 (e.g., to expose the back of the infant). It should be appreciated that the cloth cover is not limited to mesh.

Figure 2:
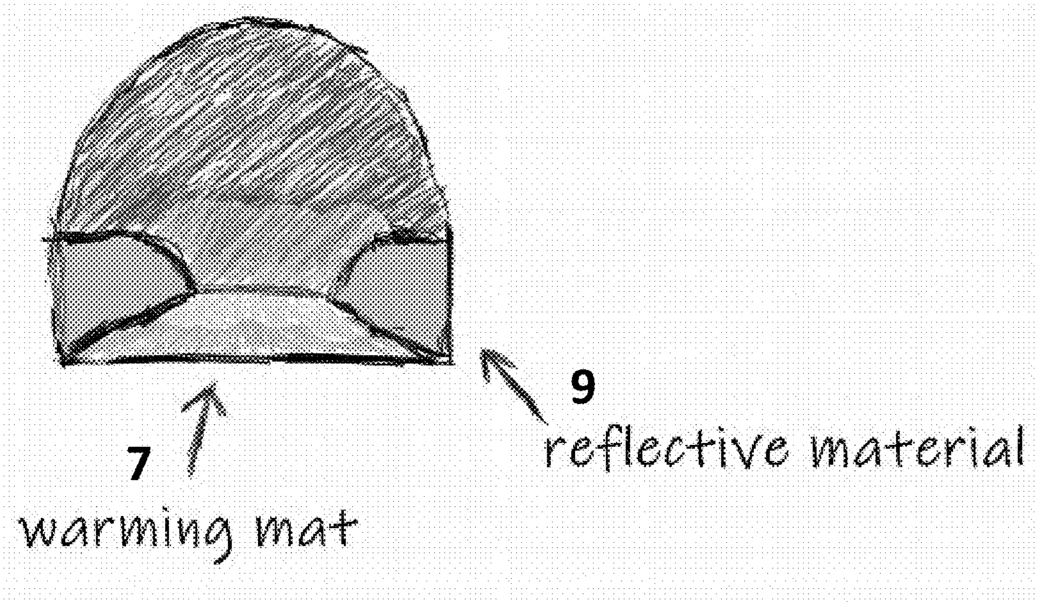
FIG. 2 is a schematic view of a portable phototherapy device, according to an alternative example embodiment of the present disclosure.

In some implementations, a pad 7 (e.g., a floatable mattress) is placed below the sheet to provide cushion to the infant 5, as shown in FIG. 2. In other words, the mattress pad 7 is a comfortable pad on which the infant 5 is placed. In some implementations, the sheet can be wrapped over the pad 7. That is, the pad 7 is placed between two sheets to form a pillow-like case.

In some implementations, the pad 7 includes a beating element (not shown) to beat the pad 7 before the infant 5 is placed in the incubator 10. The heated pad acts as a warming pad. The heating element can be a wired beating element that is disposed within the pad 7. In other implementations, the heating element can be placed below the pad 7. It should be appreciated the heating element must be connected to a power source and can only be available if plugged in.

In some implementations, the phototherapy device 1 includes a ventilation system 60 to vent or force air out of the incubator 10. That is, the ventilation system 60 helps remove air trapped in the enclosure 30 and eventually expelled out through the incubator 10. This prevents any overheating of the infant 5. For example, the ventilation system 60 ensures that the infant 5 does not exceed 100.4° F. In some implementations, the ventilation system 60 is located directly below the incubator 10. In some implementations, the ventilation system 60 can include ports to suction out the air inside the enclosure 30. The ports can be directly attached to the pad 7 to ensure sufficient expelled force is required to penetrate through the pad 7 and/or sheet.

Referring to FIG. 2, the phototherapy device 1 includes a reflective member 9 to reflect overexposure of sunlight. The reflective member 9 can be made from a material that is reflective to sunlight. For example, the reflective member 9 can be made from a metal material, such as, but not limited to, copper, silver, and/or aluminum. In another example, the reflective member 9 can be made from non-metal materials. The reflective member 9 can be located at the sides of the incubator 10 where the infant 5 rests on top of the pad 7 protecting the infant 5. In other words, the infant 5 is receiving sunlight from a top direction and not from a sideward direction.

Figure 3A:
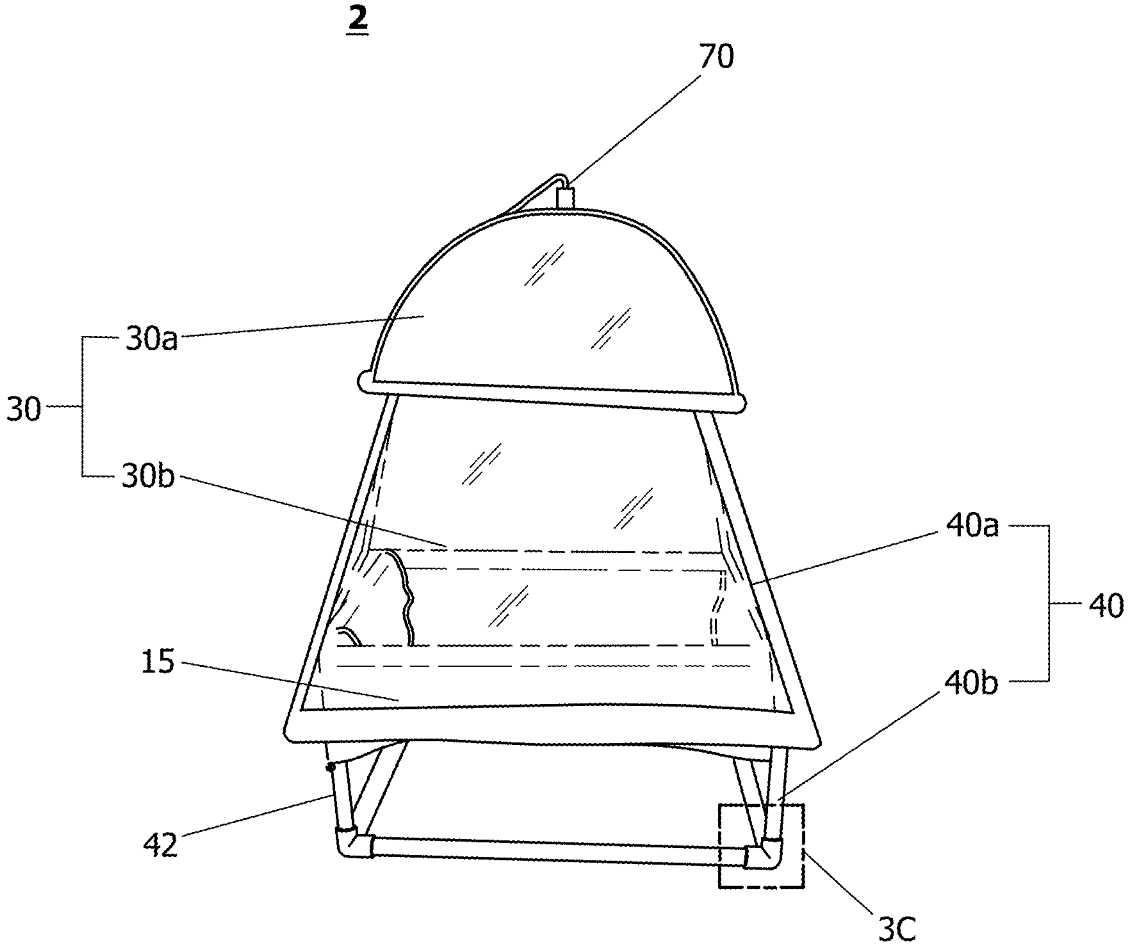
FIG. 3A is a schematic view of a portable phototherapy device, according to an alternate example embodiment of the present disclosure
Figure 3B:
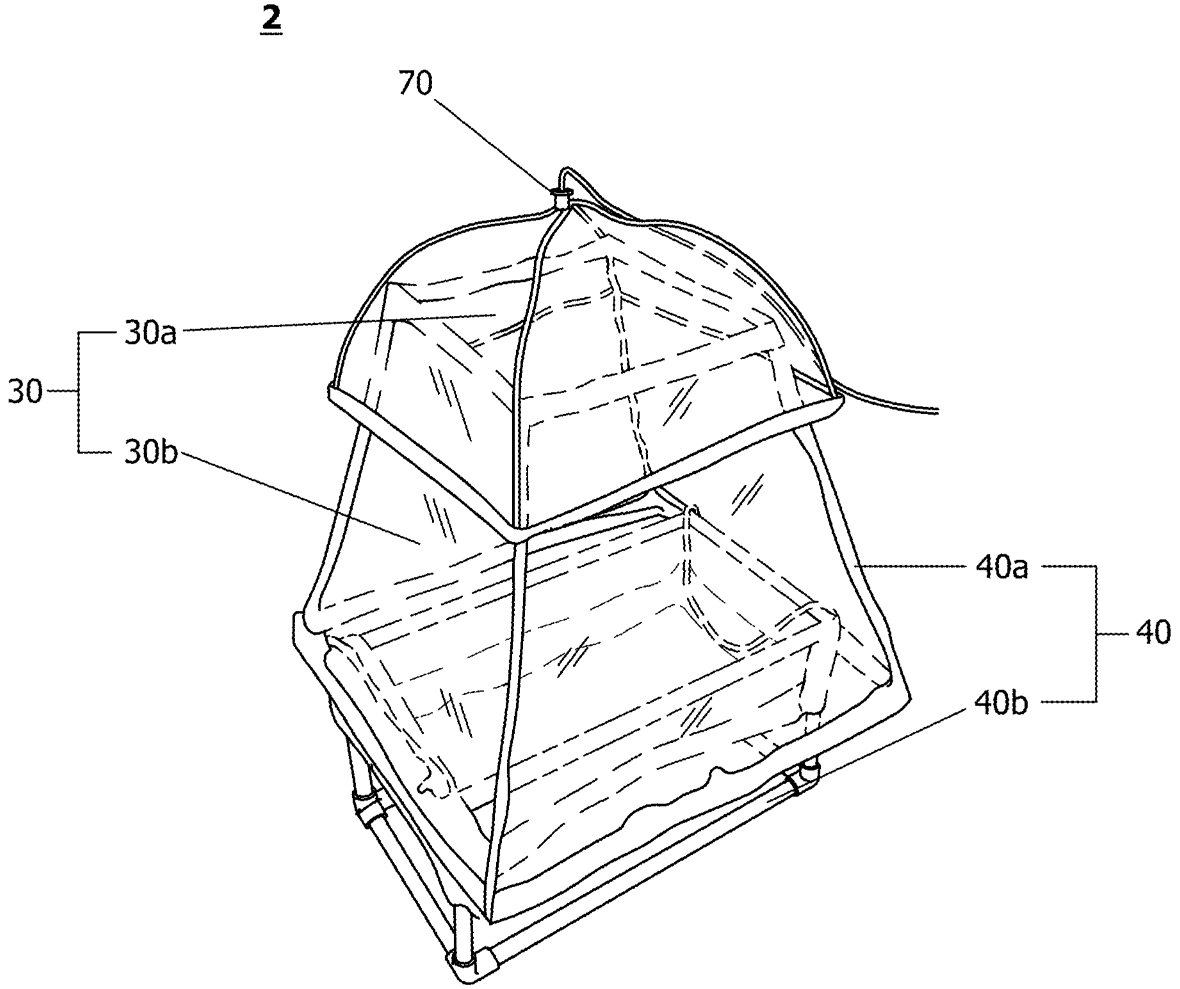
FIG. 3B is a schematic view of a portable phototherapy device, according to an alternate example embodiment of the present disclosure.

FIGS. 3A and 3B are perspective views of a portable phototherapy device 2 according to another example embodiment. FIG. 3A is a perspective view when a user looking in a perpendicular direction at the portable phototherapy device 2. FIG. 3B is a perspective view when a user looking at an angle at the phototherapy device 2.

The phototherapy device 2 includes a frame structure 40 having an upper frame portion 40*a* and a lower frame portion 40*b* and an enclosure 30 having an upper enclosure portion 30*a* and a lower enclosure portion 30*b*. The lower frame portion 40*b* is framed as a structure to hold the bassinet 15. In one implementation, the lower frame portion 40*b* is formed as a shape of a rectangle. The upper frame portion 40*a* is framed as a structure to hold (e.g., encompass, wrap) the upper enclosure portion 30*a* and the lower enclosure portion 30*b*. In one implementation, the upper frame portion 40*a* is formed as a shape of a pyramid. It should be appreciated that other shapes can be implemented as long as the upper frame portion 40*a* and the lower frame portion 40*b* are structured to hold the bassinet 15 and enclosure 30, respectively. Further, the frame structure 40 is not limited in its composition, size or shape, but has a structure to support the phototherapy device 2 in a "free-standing" configuration.

As similarly described in FIG. 1, the upper enclosure portion 30*a* and the lower enclosure portion 30*b* are made from a flexible, transparent material to filter ultraviolent (UV) and infrared radiation (IR) and prevent overexposure to the infant 5. Because the compositions or properties of the flexible transparent materials are similar, further details will not be discussed herein.

In some implementations, the upper enclosure portion 30*a* and the lower enclosure portion 30*b* are made from the same material. In other implementations, the upper enclosure portion 30*a* and the lower enclosure portion 30*b* are made from different materials. For example, the upper enclosure portion 30*a* can be made from a material that can receive the natural sunlight and filter UV and IR while the lower enclosure portion 30*b* can be made with a material that filters out the entire (i.e., reflects) sunlight. In some implementations, the upper enclosure portion 30*a* and the lower enclosure portion 30*b* have properties to be deformable. That is, the flexible material is formed of a plastically deformable material that is flexible enough to be deformed to a desired configuration by hand while also having sufficient shape memory to retain the configuration to which it has been deformed during subsequent use of the device for delivery of a light therapy session.

In some implementations, the upper enclosure portion 30*a* can be designed to separate from the lower enclosure portion 30*b*. In other words, the upper enclosure portion 30*a* can be removed with respect to the lower enclosure portion 30*b*. This feature allows heat to be removed and/or allows a caregiver to handle the infant 5 without disassembling the phototherapy device 2. In other words, the removed upper enclosure portion 30*a* allows the caregiver to reach inside of phototherapy device 2 and handle the infant 5.

The upper frame portion 40*a* and the lower frame portion 40*b* comprise a plurality of flexible rods 42 to form the structures of the upper frame portion 40*a* and the lower frame portion 40*b*. The plurality of rods 42 should be flexible, semi-rigid to rigid enough to maintain a free-standing configuration. Additionally, the plurality of rods 42 should be sturdy enough to hold the weight of the infant 5. In some implementations, the plurality of rods 42 are hollow rods made from plastic materials that is deformable and easy to cut to suitable lengths for any particular shape or design. For example, the plurality of rods 42 are non-conductive, extruded fiberglass rods having ¼ inch or ³⁄₂ inch diameter.

Figure 3C:
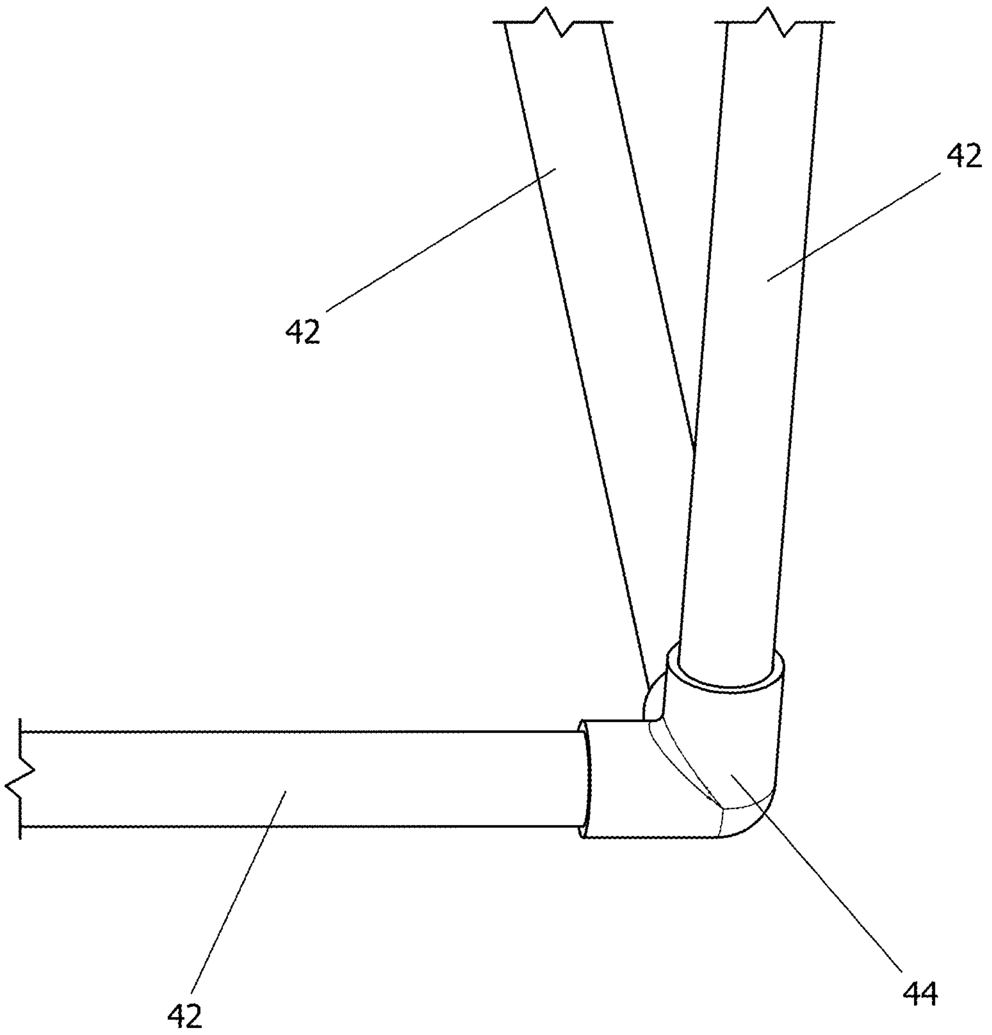
FIG. 3C is a partial view, as indicated by box A of FIG. 3A, according to an alternative example embodiment of the present disclosure.

As shown in FIG. 3C, the plurality of flexible rods 42 are used to form the structure of the lower frame portion 40*b* and assembled together via a connector 44. In other words, the connector 44 is used to form corners of the lower frame portion 40*b* (and the upper frame portion 40*a*). In some implementations, the connector 44 can be used to connect two flexible rods 42 to form a straight line to extend a length of the connected flexible rods 42. The connector 44 can be made from the same material as the plurality of rods 42, but has a slightly larger diameter to fit the plurality of rods 42 together. In other words, the connector 44 has a female fitting to connect the plurality of rods 42 having a male fitting. This provides each of the plurality of rods 42 and the connector 44 to be removable (i.e., disconnected) from each other. Because the plurality of rods 42 and connector 44 can be disconnected from each other, the phototherapy device 2, according to the present disclosure, can be disassembled for easy transport or storage when not in use.

In some implementations, as shown in FIG. 3C, a corner of the lower frame portion 40*b* is formed by a three-way connector 44 to connect the plurality of rods 42 together.

In some implementations, the plurality of rods 42 can be permanently connected to the connector 44. For example, adhesive, such as glue may be applied on an inner surface of the connector 44 to permanently connected the rods 42 to the connector 44. In other implementations, glue may be used to sufficiently hold the pieces (e.g., rods 42 and/or connector 44) together to provide a tight secure fit, rather than a permanent hold.

Similarly, the upper frame portion 40*a* can be formed using the plurality of rods 42 to form the structure of the upper frame portion 40*a*. Same pieces (e.g., rods 42 and/or connector 44) of the lower frame portion 40*b* can be used to form the upper frame portion 40*a*.

In some implementations, the upper frame portion 40*a* and the lower frame portion 40*b* can be formed in a unitary manner. In other words, the upper frame portion 40*a* and the lower frame portion 40*b* can be constructed as one-piece members.

The phototherapy device 2 can include a sensor 70. In some implementations, the sensor 70 can measure temperature inside of the phototherapy device 2. If a certain temperature is reached, an indication to alert the caregiver that the inside of the phototherapy device 2 is too warm is sent. In other implementations, the sensor 70 may send a signal to operate a ventilation unit (now shown) to either force air into the phototherapy device 2 or expel air out of the phototherapy device 2. In other implementations, the sensor 70 can measure humidity (or moisture) inside of the phototherapy device 2. Similarly, if a certain moisture is read, an alert to the caregiver is given and/or to operate the ventilation unit. In some implementations, the sensor 70 can measure vitals of the infant 5. For example, vitals include, but not limited to, temperature, blood pressure, heart rate, and respiratory rate. In some implementations, the sensor 70 can be a light measuring instrument. For example, the sensor 70 can measure an intensity of a radiation of the visible light via a filter configured to read transmission spectrum of the light. It should be appreciated that the sensor 70 can determine as one or a combination of the above mentioned operations.

In one implementation, the sensor 70 is located near the top of the phototherapy device 2. More specifically, the sensor 70 is located on top of the upper enclosure portion 30*a*. In other implementations, the sensor 70 can be located at other locations. For example, the sensor 70 can be located at any location in the lower enclosure portion 30*b* and/or on the bassinet 15.

Figure 4A:
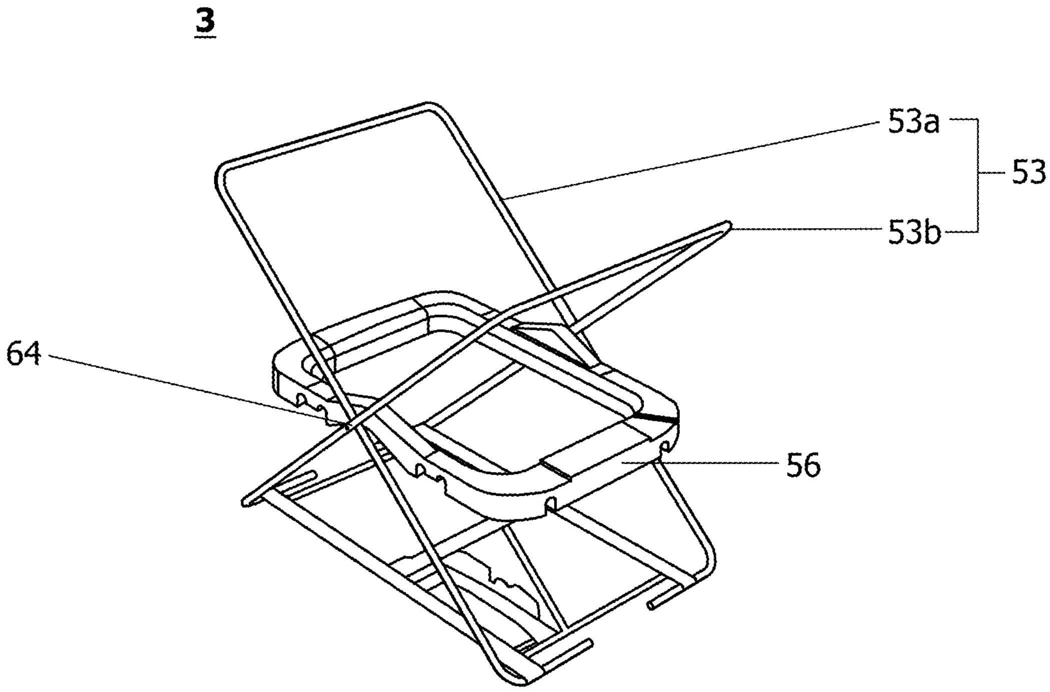
FIG. 4A is a schematic view of a portable phototherapy device, according to an alternate example embodiment of the present disclosure.
Figure 4B:
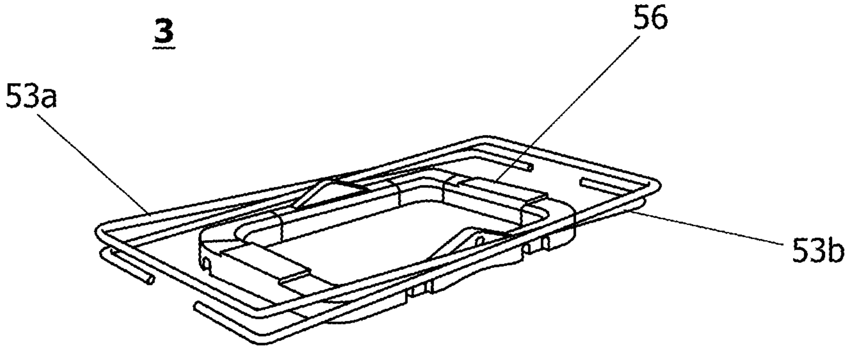
FIG. 4B is a schematic view of a portable phototherapy device, according to an alternate example embodiment of the present disclosure.

FIGS. 4A and 4B are schematic views of a phototherapy device 3 according to another example embodiment. FIG. 4A illustrates the phototherapy device 3 in a used (i.e., uncollapsed, unfolded) arrangement. FIG. 4B illustrates the phototherapy device 3 in an unused (i.e., collapsed, folded) arrangement. In this condition of FIG. 4B, the phototherapy device 3 can be easily transportable (i.e., portable) and easily stored when not in use.

The phototherapy device 3 includes a frame 53 and a bassinet holder 56. The frame 53 is designed to hold the bassinet holder 56 and the enclosure 30 (not shown). The frame 53 includes a first frame member 53*a* and a second frame member 53*b*. The frame 53 can be made from similar materials as the rods 42 described in FIGS. 3A and 3B, and thus, not discussed further in detail. The bassinet holder 56 is made from a plastic material and designed to hold the bassinet 15. For example, a mesh sheet is formed over (i.e., wraps) the bassinet holder 56 to form an area where the infant 5 can lay or rest. The frame 53 is configured to hold the bassinet holder 56.

To maintain the portable feature of the phototherapy device 3, the frame 53 is capable of being flattened, folded, compressed, or otherwise collapsed, to a size that is less than the working space of the assembled and operational phototherapy device 3 (as shown in FIG. 4A). For instance, as shown in FIG. 4B, the first frame member 53*a* and the second frame member 53*b* are "disassembled" such that the first frame member 53*a* and the second frame member 53*b* are closer to each other. In this configuration (e.g., folded or collapsed), the phototherapy device 3 can be easily transported or stored when not in use.

In some implementations, the frame 53 may be composed of poles, rods, tubes, slats, springs, or the like that can articulate, or can otherwise be positioned one to another such that they can be configured to be "assembled" (FIG. 4A) or configured to be "disassembled" (FIG. 4B). For example, a pin 64 is used to connect the first frame member 53*a* and the second frame member 53*b* together. The pin 64 acts as joint to move (i.e., rotate) the first frame member 53*a* and the second frame member 53*b*. When force is applied (e.g., downwardly), the first frame member 53*a* and the second frame member 53*b* collapse to bring the members togethers. In some implementations, a spring (not shown) can be used to create an articulation of the first frame member 53*a* and the second frame member 53*b*. That is, the spring can apply force to one or both of the first frame member 53*a* and/or the second frame member 53*b* to force the first frame member 53*a* and/or the second frame member 53*b* in an upwardly direction (i.e., assembled position or in use operation).

Figure 5A:
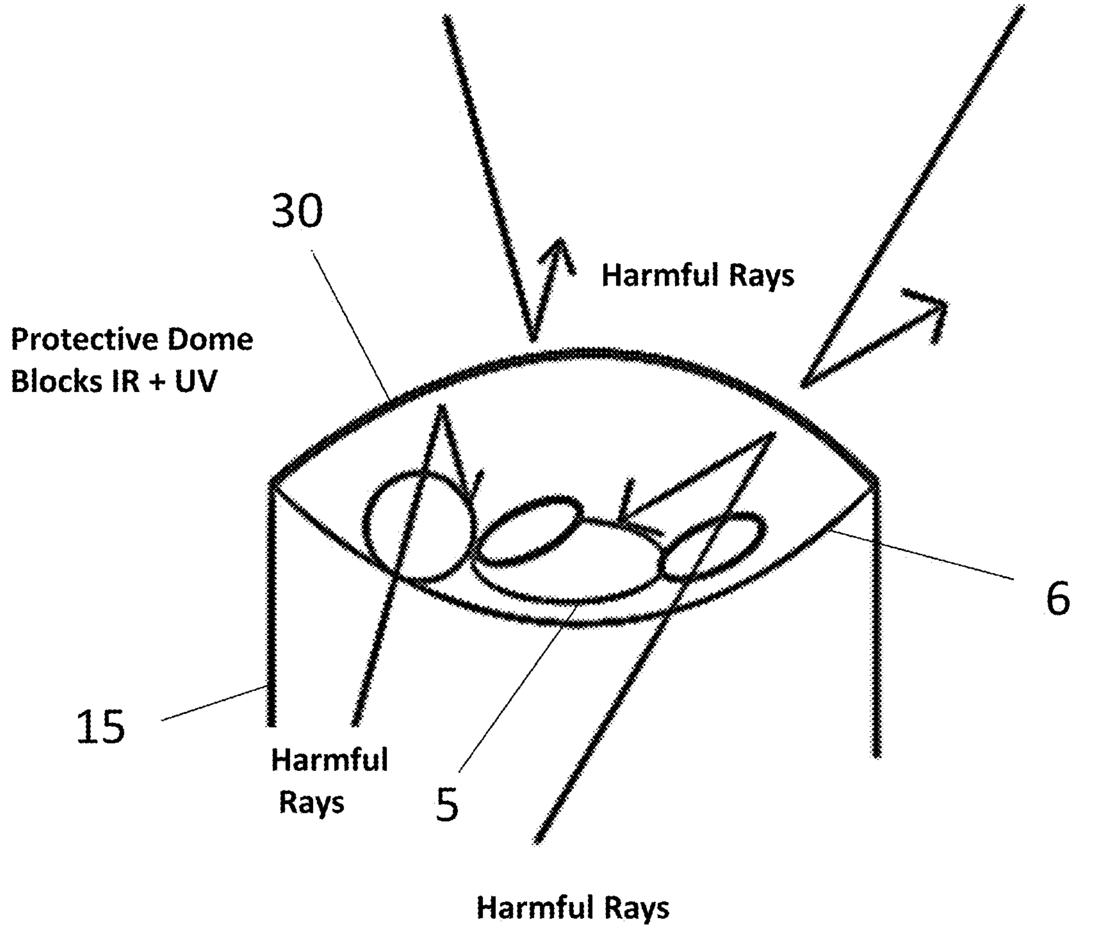
FIG. 5A is a schematic view of a configuration of an enclosure, according to example embodiments of the present disclosure.
Figure 5B:
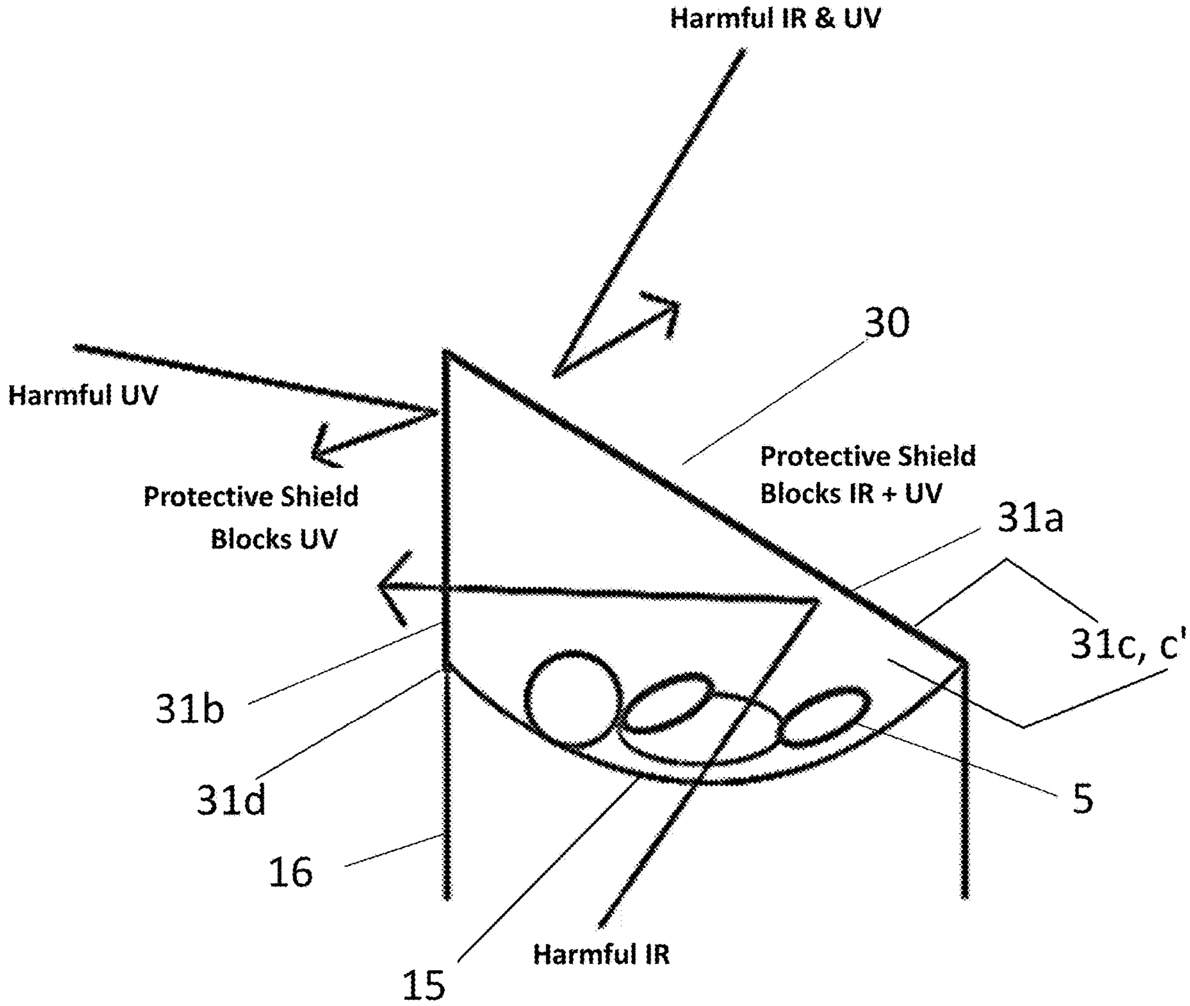
FIG. 5B is a schematic view of a configuration of an enclosure, according to example embodiments of the present disclosure.
Figure 6A:
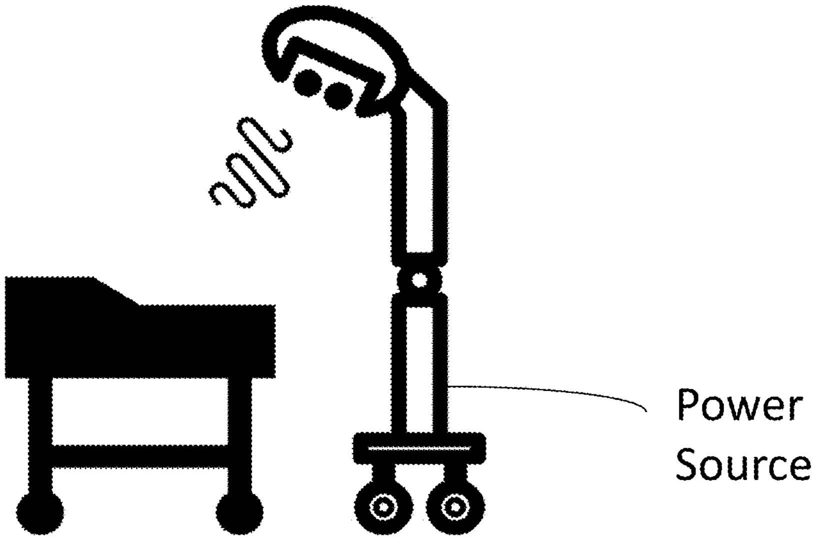
FIG. 6A CONVENTIONAL ART
FIG. 6A is a schematic view of a conventional phototherapy device.
Figure 6B:
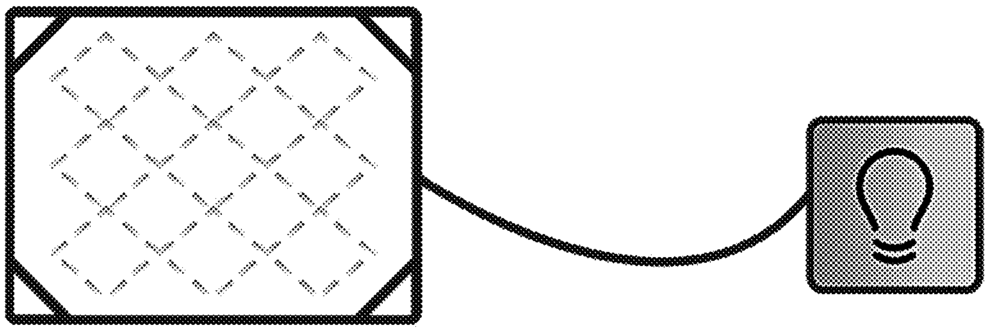
FIG. 6B CONVENTIONAL ART
FIG. 6B is a schematic view of a conventional phototherapy device.

Referring to FIG. 5A, in some implementations, the enclosure 30 can be built in a substantially circular shaped, i.e., domed. The shape of the enclosure can filter harmful IR and UV rays from entering within the enclosure 30 from the direction of the sun such that the subject 5 would be protected therein. In some implementations, a breathable material 6 can rest on top of the bassinet 15 to allow airflow therethrough within the enclosure 30. However, on some occasions, the sun isn't the only source of IR heat. For instance, IR heat may enter into the device from underneath cast off from a hot ground it was sitting on. Because the protective enclosure 30 can sometimes act as a mirror on both sides to UV and IR rays, it may on occasion trap heat radiating from the hot ground, which, as shown in FIG. 5A, is reflected off of the inner surface of the enclosure 30 and focused onto a subject therein. Therefore, one solution to this is to design a device such that IR rays outside the device cannot get in but IR rays inside the device can get out, such that there is no build-up of heat. The temperature therefore should be equal to the ambient temperature of the air. As shown in FIG. 5B, the enclosure 30 is non-symmetrically formed and lacks curved or domed surfaces. In other words, the enclosure 30 is not in a domed-like shape as compared to the device shown in FIG. 5A. In one implementation, the enclosure 30 is triangularly shaped. By changing the shape of the 'dome' to an angled shaped relative to the bassinet 15, harmful IR and UV rays can be filtered out.

In some implementations, the enclosure 30 includes a plurality of planar walls including an angled front wall 31*a* and a back wall 31*b* and corresponding opposing sidewalls 31*c* and 31*c*'. In one implementation, the back wall 31*b* is vertically formed and the angled front wall 31*a* is at an angle (e.g., 45°) with respect to the back wall 31*b*, thus, each of the vertical sidewalls 31*c* and 31*c*' are triangular. Accordingly, as depicted in FIG. 5B, the angled front wall 31*a* is at an angle of about 45° with respect to the back wall 31*b* and the angled front wall 31*a* is at an angle of about 45° with respect to a lower edge 31*d* of the enclosure 30 where it is contactable with the bassinet 15. In some implementations, the angle between the angled front wall 31*a* and the vertical back wall 31*b* is less than or equal to 45° and correspondingly the angle between the front wall 31*a* of the enclosure and the lower edge 31*d* is equal to or greater than about 45°; thus, in various implementations, the angle between the angled front wall 31*a* and the vertical back wall 31*b* can range from greater than 1° to about 45°, for example, 1, 5, 10, 15, 20, 25, 30, 35, 40, to about 45°. In some particular implementations, the angle between the angled front wall 31*a* and the vertical back wall 31*b* is about 45°.

In some implementations, the back wall 31*b* has a different material than the angled front wall 31*a*. For example, the angled front wall 31*a* can be made from a polyethylene material and the back wall 31*b* can be made from a polyethylene material including a reflective material. By having the material of the vertical formed back wall 31*b* to only block UV rays, every incident ray of IR that generates underneath the enclosure 30 will eventually find its way out of the device after no more than a few bounces. This also keeps IR and UV rays from entering from outside the device as long as the entire device is facing the equator. As such, little to no UV rays are expected to be generated by the ground underneath the device. So, therefore, trapping UV is no longer a concern. This creates a system in which ambient heat cannot build up inside the device while allowing light to enter the device which are non-harmful, useful for conjugating bilirubin and treating jaundice. In some implementations, IR rays can still enter from the back panel, however, the average ambient IR rays generation from outside objects such as trees and rocks is negligible.

EMBODIMENTS

A. A portable phototherapy device, comprising an incubator (also referred to as a bassinet) configured to hold a subject for treatment; a support 16 for supporting the incubator 15, the support 16 optionally including one or more wheels to transport the portable phototherapy device; and an enclosure 30 made from a flexible, transparent material connected to the incubator 15 to create a space therein. The enclosure 30 formed around the incubator allows visible sunlight to enter the enclosure 30 in any direction for treating the subject while partially filtering ultraviolet (UV) and infrared radiation (IR) rays of the visible sunlight. The enclosure 30 includes an angled front wall 31*a* made from a first material and a back wall 31*b* made from a second material different than the first material.

B. The device of claim A, wherein the enclosure is non-symmetrically shaped with respect to the incubator.

C. The device of claim A, wherein the enclosure is shaped as a triangle.

D. The device of claim A, wherein the angled front wall is at an angle with respect to the back wall. The device of claim A, wherein the angle is 45° with respect to the back wall of the enclosure.

E. The device of claim A, wherein the angle is at least 45° with respect to the lower edge of the enclosure and up to about 45° with respect to the back wall of the enclosure.

F. The device of claim A, wherein the flexible, transparent material is a polyethylene material.

G. The device of claim A, wherein the visible sunlight having wavelengths between 400 nm to 700 nm for treatment of the subject.

H. The device of claim D, wherein the visible sunlight having wavelengths between 380 nm to 470 nm for treatment of the subject.

I. The device of claim A, wherein the flexible, transparent material is attached to the incubator by a fastener.

J. The device of claim F, wherein the fastener is at least one of a zipper, a button, a hook-and-loop fastener, an adhesive, or a tape.

K. The device of claim A, further comprising a reflective material placed on at least one of the incubator or the flexible, transparent material.

L. The device of claim A, further comprising a ventilation system to expel air out of the incubator.

M. The device of claim A, wherein the ventilation system includes at least one port to suction out the air inside of the enclosure.

N. The device of claim A, wherein a pad is attached to the incubator for placing the subject thereon, wherein at least one port is attached to the pad for cooling the subject.

O. A portable phototherapy device, comprising: a frame including an upper frame portion and a lower frame portion, the upper frame portion and the lower frame portion include a plurality of rods, the plurality of rods being removable connected to each other; and an enclosure including an upper enclosure portion and a lower enclosure portion, the upper enclosure portion and the lower enclosure portion enclosed by a flexible, transparent material to filter ultraviolent (UV) and infrared radiation (IR), and the upper enclosure portion being separable from the lower enclosure portion, wherein the upper frame portion is framed as a structure to hold the upper enclosure portion and the lower enclosure portion, and wherein the lower frame portion is framed as a structure to hold a bassinet.

P. The device of claim L, wherein the upper enclosure portion is separable from the lower enclosure portion.

Q. The device of claim L, wherein each of the plurality of rods is a non-conductive, extruded fiberglass rod.

R. A portable phototherapy device, comprising: a frame including a first frame member and a second frame member, the first frame member and the second frame member being moveable with respect to each other causing the portable phototherapy device to be in a first configuration or in a second configuration; a support for holding a bassinet, the support positioned between the first frame member and the second frame member; and a flexible, transparent material attached to the first frame member and the second frame member to form an enclosure, the flexible, transparent material configured to filter ultraviolet (UV) and infrared radiation (IR) rays of sunlight.

S. The portable phototherapy device according to claim R, wherein: in the first configuration, the first frame member and the second frame member are closer to each other so as to be in a disassembled state, and in the second configuration, the first frame member and the second frame member are farther from each other so as to be in an assembled state.

T. The device of claim R, wherein a portion of the first frame member crosses a portion of the second frame member to pivot at a fixed point The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A phototherapy device, comprising:

a bassinet configured to hold a subject, the bassinet comprising a breathable material to allow airflow therethrough; and an enclosure configured to be placed over the bassinet, the enclosure comprising planar walls forming a triangular shape, the planar walls comprising an angled front wall and opposing sidewalls comprising a first material capable of permitting the passage of visible light and at least partially filtering ultraviolet (UV) and infrared (IR) rays, and a back wall comprising a second material different than the first material and capable of permitting the passage of visible light and at least partially filtering UV but not IR rays, wherein the enclosure lacks domed surfaces, and wherein the configuration of the planar walls directs incident IR rays out of the enclosure such that there is no build-up of heat that would harm the subject resting therein, and wherein the angled front wall is angled relative to the back wall to define an angle of about 45° therebetween.

2. The phototherapy device of claim 1, wherein the first material is a polyethylene material and the second material is polyethylene material that includes a reflective material.

3. The phototherapy device of claim 1, wherein the angle defined by the angled front wall relative to the back wall is 45°.

4. The phototherapy device of claim 1, wherein the enclosure permits passage of light having a wavelength in a range from between 400 nm and 700 nm.

5. The phototherapy device of claim 1, wherein the enclosure at least partially or fully filters the passage of light having a wavelength that is shorter than 400 nm.

6. The phototherapy device of claim 1, wherein the angled front wall and sidewalls of the enclosure at least partially or fully filter the passage of light having a wavelength that is greater than about 700 nm.

7. The phototherapy device of claim 1, wherein the back wall of the enclosure permits the passage of light having a wavelength that is greater than about 700 nm.

8. The phototherapy device of claim 1, wherein the enclosure is attached to the bassinet by a fastener.

9. The phototherapy device of claim 8, wherein the fastener is at least one of a zipper, a button, a hook-and-loop fastener, an adhesive, or a tape.

10. The phototherapy device of claim 1, further comprising a ventilation system to expel air out of the bassinet.

11. The phototherapy device of claim 10, wherein the ventilation system includes at least one port to suction out the air inside of the enclosure.

12. The phototherapy device of claim 11, wherein a pad is attached to the bassinet for placing the subject thereon, wherein the at least one port is attached to the pad for cooling the subject.

13. The phototherapy device of claim 1, comprising a support for holding and supporting the bassinet.

14. The phototherapy device of claim 13, the support comprising a material capable of permitting the passage of visible light and at least partially filtering UV and IR rays.

15. The phototherapy device of claim 13, the support comprising a material that permits passage of light having a wavelength in a range from between 400 nm and 700 nm, and at least partially or fully filters the passage of light having a wavelength that is shorter than 400 nm and greater than about 700 nm.

16. The phototherapy device of claim 13, the support comprising one or more wheels to transport the phototherapy device.

17. A phototherapy device, comprising:

a bassinet configured to hold a subject;

an enclosure configured to be placed over the bassinet, the enclosure comprising planar walls forming a triangular shape, the planar walls comprising an angled front wall and opposing sidewalls comprising a first material capable of permitting the passage of visible light having a wavelength in a range from between 400 nm and 700 nm and at least partially filtering UV having a wavelength that is shorter than 400 nm and IR rays having a wavelength that is greater than 700 nm; and a back wall comprising a second material different than the first material and capable of permitting the passage of visible light having a wavelength in a range from between 400 nm and 700 nm and IR rays having a wavelength that is greater than 700 nm and at least partially filtering UV rays having a wavelength that is shorter than 400 nm, wherein the enclosure lacks domed surfaces, and wherein the angled front wall is angled by about 45° relative to the back wall, and wherein the configuration of the planar walls directs incident IR rays out of the enclosure such that there is no build-up of heat that would harm the subject resting therein; and a support for holding and supporting the bassinet.

18. A phototherapy device, comprising:

a bassinet configured to hold a subject;

an enclosure configured to be placed over the bassinet, the enclosure comprising planar walls forming a triangular shape, the planar walls comprising an angled front wall and opposing sidewalls comprising a first material capable of permitting the passage of visible light having a wavelength in a range from between 400 nm and 700 nm and at least partially filtering UV having a wavelength that is shorter than 400 nm and IR rays having a wavelength that is greater than 700 nm; and a back wall comprising a second material different than the first material and capable of permitting the passage of visible light having a wavelength in a range from between 400 nm and 700 nm and IR rays having a wavelength that is greater than 700 nm and at least partially filtering UV rays having a wavelength that is shorter than 400 nm, wherein the enclosure lacks domed surfaces, and wherein the angled front wall is angled relative to the back wall to define an angle of 45° therebetween; and a support for holding and supporting the bassinet, the support comprising the first material capable of permitting the passage of visible light having a wavelength in a range from between 400 nm and 700 nm and at least partially filtering UV having a wavelength that is shorter than 400 nm and IR rays having a wavelength that is greater than 700 nm, wherein the enclosure and support are connectable to permit portability of the phototherapy device as a unit, and wherein the configuration of the planar walls of the enclosure directs incident IR rays out of the phototherapy device when the enclosure is connected with the support such that there is no build-up of heat that would harm the subject resting therein.

* * * * *